United States Patent
Hall et al.

(10) Patent No.: US 6,579,514 B1
(45) Date of Patent: Jun. 17, 2003

(54) ANTI INFECTIVE PERIODONTIC COMPOSITIONS

(76) Inventors: David M. Hall, 1784 Lauren La., Auburn, AL (US) 36830; James R. Hunt, 3 Dunwoody Park South, Suite 103, Dunwoody, GA (US) 30338

(*) Notice: Subject to any disclaimer, the term of this patent is extended or adjusted under 35 U.S.C. 154(b) by 0 days.

(21) Appl. No.: 10/141,232

(22) Filed: May 8, 2002

(51) Int. Cl.$^7$ .............................................. A61K 7/22
(52) U.S. Cl. ...................................................... 424/54
(58) Field of Search ...................................... 424/49–58

(56) References Cited

U.S. PATENT DOCUMENTS

| | | | | | |
|---|---|---|---|---|---|
| 4,130,637 A | * | 12/1978 | Bauman | ...................... | 424/54 |
| 4,203,872 A | * | 5/1980 | Flanagan | ................... | 510/182 |
| 4,247,538 A | * | 1/1981 | Barker | ....................... | 510/121 |
| 4,264,479 A | * | 4/1981 | Flanagan | ..................... | 134/40 |
| 4,329,334 A | * | 5/1982 | Su et al. | ................... | 424/70.19 |
| 4,329,335 A | * | 5/1982 | Su et al. | ................... | 424/70.17 |
| 4,450,091 A | * | 5/1984 | Schmolka | ................... | 510/122 |
| 4,726,944 A | * | 2/1988 | Osipow et al. | ............. | 510/120 |
| 4,839,158 A | * | 6/1989 | Michaels | ..................... | 424/54 |
| 5,225,112 A | * | 7/1993 | Miyazawa et al. | .......... | 510/124 |
| 5,244,652 A | * | 9/1993 | Michaels | ..................... | 424/54 |
| 5,389,676 A | * | 2/1995 | Michaels | ..................... | 514/556 |
| 5,645,841 A | * | 7/1997 | Hill et al. | ................... | 424/401 |
| 5,679,324 A | * | 10/1997 | Lisboa et al. | ................. | 424/45 |
| 5,736,505 A | * | 4/1998 | Manzo et al. | .................. | 512/2 |
| 5,994,383 A | * | 11/1999 | Dyer et al. | ................... | 424/54 |
| 6,087,400 A | * | 7/2000 | Dyer et al. | ................... | 514/643 |
| 6,096,349 A | * | 8/2000 | Petri et al. | .................. | 424/616 |
| 6,096,702 A | * | 8/2000 | Ramirez et al. | ............. | 510/421 |
| 6,106,817 A | * | 8/2000 | Ramirez et al. | ......... | 424/70.19 |

* cited by examiner

*Primary Examiner*—Shep K. Rose
(74) *Attorney, Agent, or Firm*—John Lezdey

(57) ABSTRACT

Periodontic compositions in gel or foam form for treating gum diseases or used in the extraction of teeth, which are alcohol free. The composition is a mixture of a tertiary amine oxide and an antimicrobial betaine compound. The composition is useful for treating gum disease and after the extraction of teeth.

13 Claims, No Drawings

ANTI INFECTIVE PERIODONTIC COMPOSITIONS

FIELD OF THE INVENTION

The present invention relates to an improvement in periodontic compositions used in connection with tooth extractions and the treatment of gum diseases by dentists. More particularly, the present invention relates to a foamable or gel anti-microbial composition, which contains a betaine compound and is free of alcohol, for use after tooth extractions and the treatment of gum diseases, especially gingivitis.

BACKGROUND OF THE INVENTION

It is desirable for uses in dentifices that a stable, rigid foam or gel be used in dentifices and in compositions used in tooth extractions and in treating gum diseases. Since P. gingervalis may not be the only microorganism involved in gum diseases, it is advisable to provide a composition having a broad spectrum of microbial kill but also a composition free of alcohols. Alcoholic compositions are considered as being potentially carcinogenic. The use of most gums or gels to improve the stability or foamability of the composition also dilutes the anti-microbial effect.

U.S. Pat. No. 4,839,158 to Michaels, which is herein incorporated by reference, discloses a dentifice containing a betaine in an alcoholic composition containing gels, gums, and the like to form a foamable product. However, the addition of such foaming agents dilutes the anti-microbial effect of the composition and the foam produced is not stable for a sufficient length of time.

U.S. Pat. No. 5,389,676 to Michaels, which is herein incorporated by reference, discloses anti-infective water-in-oil or oil-in-water compositions comprising amphoteric surfactants of amine oxides, hydrophobic materials and emulsion aids, which can be used as a dentifice. The compositions containing gelatins to improve Bloom strength which result in a dilution of the antimicrobial effect.

U.S. Pat. Nos. 4,062,976, 4,075,350, 4,127,328, 4,183,852, and 4,837,158 disclose amphoteric betaine and amine oxide compositions but not those with a stable foam.

SUMMARY OF INVENTION

The present invention relates to an anti-infective, foamable periodontic composition which is free from alcohols, which can be used in tooth extractions and gum diseases. More particularly, there is provided a foamable composition comprising an ethoxylated tertiary amine in combination with a betaine.

The composition contains about 0.1 to 10% of mixture of the betaine and the ethoxylated tertiary amine in combination with optional fillers. Preferably, the composition comprises a ratio of about 1 to 1:5 of betaine to amine compound, preferably 3:1.

Advantageously, the final composition has a pH between 4.8 and 7.8.

Advantageously, the viscosity of the final composition can be adjusted utilizing a salt solution, preferably, sodium chloride, or zinc chloride.

It is therefore a general object of the invention to provide an anti-infective gel or foamable periodontic composition having a broad spectrum of antimicrobial activity.

It is a further object of the invention to provide a foamable periodontic composition having good foaming characteristics which viscocity can be controlled with a salt solution.

It is yet another object of the invention to provide a composition to prevent staining of tooth enamel. It is still a further object of the invention to provide a foamable periodontic composition whose viscocity is adjustable by pH or the addition of a salt solution.

It is a further object of the invention to treat a patient suffering from a gum disease.

DESCRIPTION OF THE PREFERRED EMBODIMENTS

In accordance with the invention there is provided an anti-infective foamable periodontic composition, which is foamable without the use of foaming aids and gelatins.

More particularly, there is provided a periodontic composition comprising about 0.1 to 10.0 weight percent of a mixture of a betaine and an ethoxylated tertiary amine wherein the betaine compound is in a ratio to the ethoxylated tertiary amine of 1:5 to 5: 1, preferably about 3:1. The high foaming characteristics of the composition provides longer antimicrobial activity and improved adherence to the gums and teeth.

The ethoxylated tertiary amine oxides of the invention have the general formula:

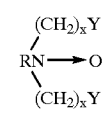

I

Wherein R is an alkyl group having 2 to 18 carbon atoms, x is an integer of 1 or 2, and y is hydrogen or hydroxy.

Preferred are the compounds of formula I having a molecular weight greater than 250. Suitable compounds include N,N-dialkyl-1-hexadecanamine oxide, for example, N,N-dimethyl-1-hexadecanamine oxide; N,N-dimethyl-1-octadecanamine oxide, for example N,N-dimethyl-1-octadecanamine oxide; bis(2-hydroxy methyl-1-amine oxide); bis(2-hydroxy methyl-1-propyl amine oxide); and the like.

Illustrative of the betaine are: (1)coco-N-betaine, cetyl-N-betaine, stearyl-N-betaine, isostearyl-N-betaine, oleyl-N-sulfobetaine; and (3) cocoamido-N-betaine, cetylamido-N-betaine, stearylamido-N-betaine, isostearylamido-N-betaine, oleyl-amino-N-betaine, and the like.

When used here the term "coco" is that used in the CTFA (designations of Cosmetic and Toiletry and Fragrance Association, Wash., D.C.) and is used to indicate alkyl groups present in coconut oil, i.e. a mixture of alkyl groups from 10 to 18 carbon atoms. The designations of the compounds listed herein are those of the CTFA.

Preferably, the betaines used in this invention are selected from the group consisting of (a) alkyl-N-sulfobetaines, acyl-N-betaines, and mixtures of two or more thereof The term betaine when used herein means N-dimethyl glycine and its lower alkyl homologs. Unless otherwise specified an N-dimethyl compound is intended. The term sulfobetaine or sultaine means the sulfuric acid analog of such betaines.

Typically, the betaine and amine oxide components are present in a molar ratios of from 1:5 to 5:1, preferably, in a molar ratios of about 1:1. In general, the acid necessary, when necessary to supply the required pH to the amphoteric surfactants can be any organic or inorganic acid, such as hydrochloric acid, phosphoric acid, sulfuric acid, citric acid, acetic acid, or nicotinic acid. The operating pH for the surfactant composition is 4:5 to 7:0 preferably, from about 4.5 to 6.5. The pH of an aqueous solution comprising the above enumerated components is determined by employing an aqueous solution of 0.5%, by weight, total of active components typically at a glass electrode, to precisely define the acidity.

The compositions of the invention can be foamed utilizing conventional foaming devices. The viscocity of the foam can be controlled by pH change or by salt addition, for example, sodium chloride, zinc chloride or zinc gluconate. The foamed composition can be formed in situ to either treat a patient with a tooth extraction or with gum disease.

For use in tooth extracted patients the composition can contain pain killers such as lidocaine, alpha$_1$-antitrypsin, or the like.

Hyaluronic acid acts both as a thickening agent and as a wound healer so that it is particularly preferred for use in tooth extractions.

If additional thickening agents are required, it is preferable to use carogeenan gum which is also antimicrobial or other natural antimicrobail gums. The additional fillers or ingredients can be used in an amount of about 0.1 to 10% by weight of composition.

The foamed compositions are particularly useful in tooth extractions so as to heal without bacterial contamination from the mouth. The gel is useful especially in the treatment of gum disease and can be combined with conventional tooth paste.

The following examples illustrating the composition of the invention are not intended to limit the scope of the invention.

EXAMPLE 1

A formula was prepared by admixing the following:

| Ingredients | Parts by Weight |
| --- | --- |
| Lauryl Betaine | 100.0 |
| N,N-dimethy-1-hexadecanamine oxide | 80.9 |
| Citric Acid monolydiate | 6.3 |
| Purified Water | 10.0 |

The composition can be placed into a foam and used for the treatment of gingivitis.

EXAMPLE 2

A foamable composition was prepared by admixing the following:

| Ingredients | Parts by Weight |
| --- | --- |
| Cetyl Betaine | 90.0 |
| Bis(2-hydroxyethylpropyl amine oxide) | 100.0 |
| Purified Water | 10.0 |

The pH of the composition was adjusted to 5.0 with citric acid. The composition can be used when extracting teeth.

EXAMPLE 3

A gel composition can be prepared by admixing the following:

| Ingredients | Parts by Weight |
| --- | --- |
| N,N-dimethyl-1-octadecanamine oxide | 1.2 Kg |
| Cetyl Betaine | 0.6 Kg |
| Purified Water | qs. |
| | 10 Kg |

Sufficient water was used to produce 10 Kg of mixture. The mixture formed a gel which can be used in the treatment of gingivitis.

EXAMPLE 4

A gel composition can be prepared by admixing the following:

| Ingredients | Parts by Weight |
| --- | --- |
| Cetyl Betaine | 35 g |
| Coco hydroxy propyl solution | 37 g |
| Carageneenan | 2 g |
| Citric acid monohydrate | 9 g |
| Purified Water | 10 g |
| Bis(2-hydroxyethyl-1-propylamine oxide) | 36 g |

EXAMPLE 5

A foamable composition an be prepared by admixing the following:

| Ingredients | Parts by Weight |
| --- | --- |
| Cetyl Betaine | 76.5 g |
| Bis(2-hydroxyethyl-1-octadecamine oxide) | 36.5 g |
| Purified Water | 40.0 g |

EXAMPLE 6

The formulation in Example 1 was formed in a foam generator and compared to the foam characteristics of the foams obtained when the amine oxide employed was decyl-N,N-dimethylamine oxide, lauryl-N,N-dimethylamine oxide, cetyl N,N-dimethylamine oxide, oleyl N,N dimethylamine oxide, stearyl N,N-dimethylamine oxide and myristamines. The foam generated employing the compound in example 1 gave a more copious and more stable foam than any of the other amine oxide combinations.

| Microorganism | Optical Density (600 nm at various dilutions | | | | |
| --- | --- | --- | --- | --- | --- |
| Anaerobic | 1/2 | 1/20 | 1/200 | 1/2,000 | 1/20,000 |
| T. denticola | 0.0 | 0.0 | 0.54 | 0.5 | 0.58 |
| P. intermedia | 0.0 | 0.0 | 0.47 | 0.58 | 0.34 |
| P. gingivalis | 0.0 | 0.45 | 0.7 | 0.65 | 0.76 |
| Microaerophilic | 1/2 | 1/20 | 1/200 | 1/2,000 | 1/20,000 |
| A. a | 0.0 | 0.0 | 0.57 | 0.58 | 0.77 |
| Facultative | 1/2 | 1/20 | 1/200 | 1/2,000 | 1/20,000 |
| S. sanguis | 0.0 | 0.0 | 0.4 | 0.36 | 0.45 |
| S. mutans | 0.0 | 0.0 | 0.43 | 0.57 | 0.52 |
| A. viscosus | 0.0 | 0.0 | 0.22 | 0.24 | 0.41 |
| A. naselundii | 0.0 | 0.0 | 0.84 | 0.97 | 0.94 |

COMPARATIVE EXAMPLE 1

A formulation was prepared according to U.S. Pat. No. 5,389,676 comprising:

| Ingredients | Parts by Weight |
| --- | --- |
| Lauryl Betaine | 100.0 |
| Lauramine Oxide | 80.9 |
| Citric Acid monohydrate | 6.3 |
| Purified Water | 10.0 |

The formulation was placed in a foam generator and foamed into a 100 ml cylinder. The foam generated in Example 6 was placed in an adjacent 100 ml cylinder. After 5 minutes the columns were compared. The foam generated by the formulation of comparative Example 1 began dissipate. The foam generated in Example 6 remained stable and rigid.

COMPARATIVE EXAMPLE 2

Following the procedure of comparative Example 1, two columns of foam were prepared. To each of the columns was added 10% by weight of sodium chloride.

Results

The foam of the composition from comparative Example 1 dissipated immediately while the foam of the formulation of Example 6 remained rigid.

What is claimed is:

1. In an aqueous foamable periodontic composition containing at least one antimicrobial betaine compound the improvement which comprises said composition containing a surfactant which is a tertiary amine oxide of the formula:

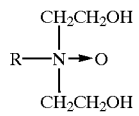

wherein R is an alkyl or alkoxy group having 2 carbon atoms, said composition being free of alcohol.

2. The composition of claim 1 wherein the composition has a pH between 4.8 and 7.0.

3. The composition of claim 1 wherein said betaine compound is selected from the group consisting of alkyl sultaine, alkyl amide, ethyl betaine, alkyl amide propyl betaine, alkyl-N-betaine, alkyl ethyl amide propyl hydroxyl sultaine, alkyl hydroxyl propyl sultaine, alkyl-N-betaine.

4. The composition of claim 1 wherein said betaine compound is selected from the group consisting of cetyl betaine and lauryl betaine.

5. The composition of claim 1 which is a gel.

6. The composition of claim 1 which is a foam.

7. The composition of claim including hyaluronic acid.

8. The composition of claim 1 including a carageenan gum.

9. The composition of claim 1 including a salt selected from the group consisting of sodium chloride, zinc chloride, and zinc gluconate.

10. A method of treating a patient having a gum disease which comprises administering a therapeutically effective amount of the composition of claim 1 to treat said gum disease.

11. A method of treating a patient having a gum disease which comprises administering a therapeutically effective amount of the composition of claim 5 treat said gum disease.

12. A method of treating a patient after tooth extraction which comprises administering an effective amount of a foamed composition of claim 1 to treat said patient.

13. The composition of claim 1 wherein R is an ethoxy group.

* * * * *